United States Patent
Breckon (10) Patent No.: US 10,166,359 B2
(45) Date of Patent: Jan. 1, 2019

(54) CONNECTOR FOR RESPIRATORY DUCTS

(71) Applicant: INTERSURGICAL AG, Vaduz (LI)

(72) Inventor: Laura Elizabeth Breckon, Wokingham (GB)

(73) Assignee: Intersurgical AG, Vaduz (LI)

(*) Notice: Subject to any disclaimer, the term of this patent is extended or adjusted under 35 U.S.C. 154(b) by 526 days.

(21) Appl. No.: 14/384,104

(22) PCT Filed: Mar. 8, 2013

(86) PCT No.: PCT/EP2013/054791
§ 371 (c)(1),
(2) Date: Sep. 9, 2014

(87) PCT Pub. No.: WO2013/132086
PCT Pub. Date: Sep. 12, 2013

(65) Prior Publication Data
US 2015/0040898 A1 Feb. 12, 2015

(30) Foreign Application Priority Data
Mar. 9, 2012 (GB) .................... 1204196.8

(51) Int. Cl.
*A61M 16/08* (2006.01)
*A61M 39/10* (2006.01)
(Continued)

(52) U.S. Cl.
CPC ...... *A61M 16/0816* (2013.01); *A61M 16/009* (2013.01); *A61M 16/0078* (2013.01);
(Continued)

(58) Field of Classification Search
CPC .......... A61M 16/0427; A61M 16/0429; A61M 16/0434; A61M 16/0445; A61M 16/0461;
(Continued)

(56) References Cited

U.S. PATENT DOCUMENTS 3,922,011 A * 11/1975 Walters ................ F16L 37/088
285/277
4,152,017 A    5/1979 Abramson
(Continued)

FOREIGN PATENT DOCUMENTS

| GB | 2020384 A | 11/1979 |
| GB | 2033543 A | 5/1980 |
| WO | 9815304 A1 | 4/1998 |

OTHER PUBLICATIONS

International Search Report and Written Opinion for corresponding Application No. PCT/EP2013/054791 (dated Jun. 3, 2013).
(Continued)

*Primary Examiner* — Annette Dixon
(74) *Attorney, Agent, or Firm* — LeClairRyan PLLC (57) ABSTRACT

The invention concerns a connector for connecting respiratory ducts together such that they are placed in fluid communication. The connector comprises a first conduit having a female connector end and a second conduit having a male connector end adapted to be received within the female connector end of the first conduit such that the male and female connector ends form a common conduit having an inner surface formed at least in part by the male connector end. The male connector has a retaining formation which is adapted to abut a corresponding formation of the female connector so as to resist separation of the first and second conduits while permitting relative rotation there-between when connected. The inner surface of the male connector may comprise a gas washed surface in use. The engagement formation is preferably a recessed area of the female connector, which may be generally annular in shape. In one embodiment, the member(s) may comprise a valve seat. The invention also concerns a breathing circuit comprising the connector.

21 Claims, 7 Drawing Sheets

(51) Int. Cl.
*F16L 27/08* (2006.01)
*F16L 37/53* (2006.01)
*A61M 16/00* (2006.01)
*F16L 37/098* (2006.01)
*A61M 16/06* (2006.01)
*A61M 16/20* (2006.01)

(52) U.S. Cl.
CPC ........ *A61M 16/0084* (2014.02); *A61M 16/06* (2013.01); *A61M 16/0825* (2014.02); *A61M 16/0833* (2014.02); *A61M 16/0875* (2013.01); *A61M 16/0883* (2014.02); *A61M 16/201* (2014.02); *A61M 39/10* (2013.01); *A61M 39/1011* (2013.01); *A61M 39/1055* (2013.01); *F16L 27/0816* (2013.01); *F16L 37/098* (2013.01); *F16L 37/53* (2013.01); *A61M 16/208* (2013.01); *A61M 2039/1072* (2013.01); *A61M 2202/0208* (2013.01); *A61M 2202/0283* (2013.01)

(58) Field of Classification Search
CPC .......... A61M 16/0463; A61M 16/0465; A61M 16/0488; A61M 16/08; A61M 16/0816; A61M 16/16; A61M 16/209; A61M 2039/1027; A61M 2039/1033; A61M 2039/1061; A61M 2039/1088; A61M 2039/242; A61M 2039/2433; A61M 2039/246; A61M 2205/273; A61M 2205/32; A61M 2210/0618; A61M 2230/005; A61M 25/0014; A61M 39/00; A61M 39/0613; A61M 39/10; A61M 39/1011; A61M 39/1055; A61M 39/22; A61M 39/221; A61M 39/24; A61M 39/26; A61M 5/348; F16K 15/147; F16K 15/20; F16L 15/08; F16L 19/0218; F16L 19/025; F16L 23/032; F16L 27/0804; F16L 27/082; F16L 29/00; F16L 37/025; F16L 37/084; F16L 37/088; F16L 37/0982; F16L 37/0987; F16L 37/113; F16L 37/36; F16L 37/373; F16L 37/53
USPC .... 128/200.13, 207.14, 207.15, 207.18, 912; 285/147.1, 24, 260, 272, 275, 277, 280, 285/281, 315, 319, 321, 332, 347, 351, 285/354, 386, 39, 417, 423, 902, 921
See application file for complete search history.

(56) References Cited

U.S. PATENT DOCUMENTS

| | | | | |
|---|---|---|---|---|
| 4,256,099 | A | * 3/1981 | Dryden | A61M 16/0463 128/200.26 |
| 4,580,816 | A | * 4/1986 | Campbell | A61M 39/00 285/321 |
| 4,676,241 | A | * 6/1987 | Webb | A61M 16/08 128/207.14 |
| 4,844,512 | A | * 7/1989 | Gahwiler | F16L 37/084 285/275 |
| 4,875,718 | A | 10/1989 | Marken | |
| 4,905,964 | A | * 3/1990 | Shiozaki | F16L 37/0982 251/149.6 |
| 4,981,586 | A | * 1/1991 | Bartholomew | F16L 37/0987 210/435 |
| 4,991,882 | A | * 2/1991 | Gahwiler | F16L 37/084 285/319 |
| 5,104,157 | A | * 4/1992 | Bahner | F16L 37/084 285/307 |
| 5,113,571 | A | * 5/1992 | Manska | A61M 39/10 285/332 |
| 5,607,139 | A | * 3/1997 | Kjellberg | F16L 37/42 251/149.1 |
| 5,738,143 | A | * 4/1998 | Faughn | F16L 37/373 137/614.03 |
| 5,775,741 | A | * 7/1998 | Rice | E04H 4/1663 15/1.7 |
| 5,799,986 | A | * 9/1998 | Corbett | B29C 45/1671 285/133.21 |
| 2006/0025751 | A1* | 2/2006 | Roy | A61M 5/348 604/523 |
| 2008/0140054 | A1* | 6/2008 | Lee | A61M 39/1055 604/533 |
| 2008/0277610 | A1* | 11/2008 | Bahner | F16L 37/38 251/148 |
| 2008/0277919 | A1 | 11/2008 | Valentini | |
| 2011/0155135 | A1 | 6/2011 | Chiu | |

OTHER PUBLICATIONS

Search Report for corresponding Application No. GB1204196.8 (dated Jun. 11, 2012).

* cited by examiner (a)

CONNECTOR FOR RESPIRATORY DUCTS

This application is a national stage application under 35 U.S.C. § 371 of PCT Application No. PCT/EP2013/054791, filed Mar. 8, 2013, which claims the priority benefit of Great Britain Application No. 1204196.8, filed Mar. 9, 2012.

FIELD OF THE INVENTION

This invention relates to connectors for respiratory ducts and, more particularly, although not exclusively, to connectors which allow relative rotation between two connected ducts.

BACKGROUND OF THE INVENTION

Breathing circuits may comprise a number of respiratory tubes which are connected together to form a primary gases passageway. Secondary devices may need to be connected to the primary gases passageway, for example via ports in the side wall thereof. The various parts of the circuit are typically connected by connectors having standard fittings to allow male or female tube fittings to be connected thereto.

It is desirable to be able to change the relative orientations of the connected parts in a number of situations. For example, in the case where a connected secondary device includes an elongate element such as a tube, the elongate element may interfere with the work of the clinician during treatment of the patient. There exist a number of other scenarios in which it may be desirable to reorient connected tubing or devices, such as to prevent interference with a view of, or access to, further components of the system or other equipment. It may therefore be advantageous to re-orientate one or more connected member relative to the primary gases passageway so that the elongate element no longer interferes.

If standard connectors are used, changing the orientation of one part relative to another typically requires the part to be disconnected from the circuit and reconnected in a different orientation. Thus standard connectors typically only allow relative rotation between the components when disconnected or else during connection, but not when the desired secure connection has been achieved. This process of disconnection and reconnection allows unwanted atmospheric gases into the circuit. Also, the twisting and reconnection of tubes, for example with a friction fit, introduces residual stress in the system which can potentially lead to loosening of the connection or else kinking within a tube, thereby restricting flow along the tube.

Figure 1:
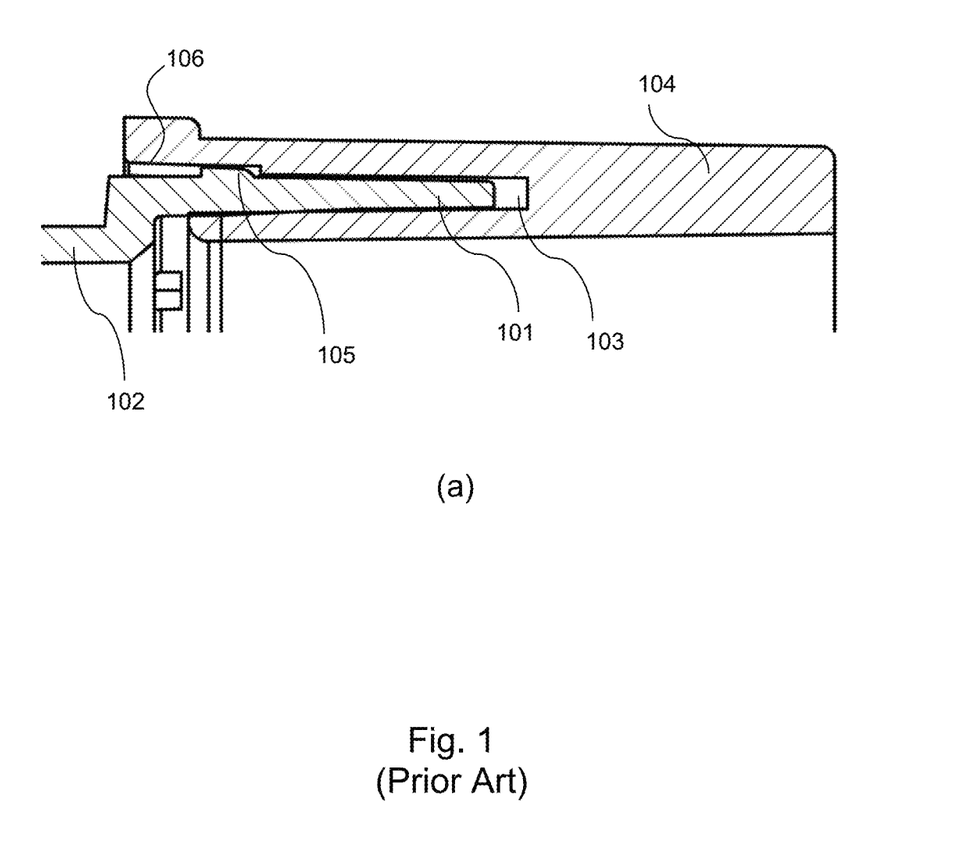
FIG. 1 shows a prior art "swivel" connector.

Existing rotating connectors, commonly referred to as "swivel" connectors, typically comprise two tubular conduits connected together and which are able to rotate relative to each other. FIG. 1 shows a prior art swivel connector. This shows a connector comprising an open connector end 101 of a first tube 102 received within an annular recess 103 located in the side wall of a second tube 104.

The annular recess encloses the connector end 101 of first tube 102 such that the desired relative positioning is achieved and a projection 105 on the connector end 101 maintains the end within annular recess 103. A plurality of circumferentially spaced abutments (not shown in FIG. 1) depend inwardly from the inwardly facing wall 106 of the second tube 104 at its open end in order to prevent removal of the connector end 101 from the annular recess 103.

Connectors of the type shown in FIG. 1 have been found to be inadequate for the purpose for re-orientating a component of a circuit such that it remains in a position in which it does not interfere with the treatment of a patient by a clinician. That is to say, any residual stress in the connected second tube 104, after re-orientation, will cause the tube 104 to return to its previous position, thereby requiring the connected tube to be moved repeatedly to its desired location, which can be both a distraction and an annoyance to the operator or clinician.

It has been found that the connector of the type shown in FIG. 1 can become disconnected. Thus, whilst the connector can prevent the connector end 101 being removed from the annular recess in normal use, there exists the possibility that the end could accidentally become disconnected upon application of sufficient tension to second tube 104 or else a bending moment about the connection.

Furthermore, whilst the connector arrangement of FIG. 1 is suitable for some simple types of connectors, such as elbow connectors or the like, the connector may not be suitable for other scenarios, such as, for example, when a secondary device is connected to the main gas passageway via the connector.

SUMMARY OF THE INVENTION

It is an aim of the present invention to provide a connector which overcomes or mitigates some or all of the above mentioned disadvantages associated with the prior art. It may be considered to be an aim of the invention to provide a connector which allows for relative reorientation of connected ducts in scenarios which cannot be accommodated by conventional swivel connectors.

BRIEF DESCRIPTION OF THE DRAWINGS

A preferred embodiment of the invention will now be described, for illustration only, with reference to the accompanying drawings, in which:

FIGS. 4(a) and (b) show longitudinal sections of the assembled connector according to the invention;

FIG. 7(b) is a partial section in a plane which contains a window.

DETAILED DESCRIPTION OF THE INVENTION

According to a first aspect of the invention there is provided a connector for connecting respiratory ducts together such that they are placed in fluid communication, the connector comprising a first conduit having a female connector end and a second conduit having a male connector end adapted to be received within the female connector end of the first conduit such that the male and female connector ends form a common conduit having an inner surface formed at least in part by the male connector end, wherein the male connector has a retaining formation which is adapted to abut a corresponding formation of the female connector so as to resist separation of the first and second conduits whilst permitting relative rotation thereof when connected.

The arrangement of the connector such that the male connector end defines at least part of the flow passage through the conduit is particularly beneficial in that it allows the connector to accommodate a number of connector scenarios in which the connector shown in FIG. 1 would be unsuitable.

The inner surface of the male connector may comprise a gas washed surface in use.

When the male connector is received within the female connector, the common conduit of the connector typically defines a gases passageway. The female conduit preferably comprises a side wall. In use, the retaining formation may be adapted to engage the corresponding formation on the inner surface of female connector in order to inhibit relative axial movement between the male and female connector portions. However, rotational motion of the male conduit relative to the female conduit is not inhibited. The corresponding formation on the female connector may be referred to as an engagement formation.

The corresponding formation is preferably a recessed area of the female connector, for example an area of the connector wall having a reduced thickness relative to at least an adjacent area of the wall. The recessed area may be generally annular. The recessed area preferably lies in the plane of the principal axis of the first conduit.

The depth of the recessed area may be between 0.1 and 0.5, typically between 0.2 and 0.4, of the wall thickness.

The recessed area may be at least partially defined by a lip, flange or intermediate wall portion adjoining the recessed area to the adjacent area of the female connector wall. The intermediate wall portion may provide an end stop or abutment formation for the retaining formation of the male connector.

One or more apertures may be provided in the female connector wall. The, or each, aperture may be provided in the vicinity of the corresponding formation. The one or more apertures may open into the recessed area of the female connector.

There is preferably a plurality of apertures in the female connector wall. The apertures may be symmetrically disposed about the axis of the connector. The, or each, aperture may be elongate and is preferably rectangular. The, or each, aperture may extend in a circumferential direction. There are preferably four apertures. The female connector may have one or more depressions, for example on an internal surface thereof and the apertures may be located between the depressions.

At least a portion of the retaining formation may be raised with respect to an outer surface of the male connector end. The retaining formation is preferably annular and may be an annular flange. The annular recess of the female conduit may be adapted to receive the annular flange on the male connector end. In use, if a user attempts to pull the male and female conduits apart, the flange abuts the recessed area, inhibiting further movement.

The flange may project radially outwardly from the surface of the plug. The flange may have a smooth outer surface so that friction with the recessed area of the female conduit is reduced.

In one embodiment, the retaining formation may also serve as a seal member. The retaining formation may contact the female connector in a manner which substantially prevents escape of respiratory gases at the interface between the male and female members. Both an outwardly facing surface and also a side surface of the retaining formation may provide a sealing effect in combination with the opposing formation in the female connector. This is in contrast to the arrangement of FIG. 1, in which the gas seal is performed by a friction or interference fit between the inner surface of connector end 101 and the opposing wall of the annular recess 103. That seal is thus defined by a relatively large contact area between those opposing surfaces. Accordingly, the prior art arrangement typically requires silicone grease to be provided at the interface such that the opposing connector parts can swivel in use. The present invention may advantageously avoid the need for such lubricating materials.

Additionally or alternatively a seal formation may be provided on either the male or female connector at an interface between those components. For example an annular sealing lip or flange may be provided on an outer surface of the male connector, or else an inner surface of the female connector, to engage a correspondingly shaped, typically annular, portion of the other connector.

In one embodiment, the ratio of the diameter to the length of the male connector is less than 1.4. The ratio of the diameter to the length of the male connector received within the female connector may be less than 1.4. In either embodiment, the ratio may be less than 1.3 or 1.2 and may be in the region of 1.0 such that the length of the male connector may be substantially equal to its diameter. This has been found to provide a particularly secure connection.

This is advantageous since, for a given diameter, the male connector extends further into the female connector than in prior art connectors. This means there is a greater contact area between the outer surface of the male connector and the inner surface of the female part. This means that the friction between the male and female parts is greater than in prior art connectors. The greater friction means that the male part can be placed in a particular orientation relative to the female part and remain in that orientation stably, without the need to disconnect any component of the circuit.

Furthermore, due to the greater length of male connector, it is much less likely to become accidentally detached from the female part than in prior art systems.

The male connector may be provided with an end stop which is adapted to engage with the end of the female connector to limit the extent to which the male connector may enter therein. The end stop may project radially outwardly from the surface of the male connector. The end stop may comprise an annular shoulder.

In one embodiment, which is in many ways preferred, the male connector end may have a member, such as an arm or limb, extending into or across the second conduit. The member may be a cross-member and may thus extend into the flow path through the second conduit in use. The member may be substantially perpendicular to the direction or axis of the second conduit. A plurality of said members may be provided, each of which may be angularly offset, for example about an axis of the second conduit. A pair of members may be provided in a perpendicular or cross configuration.

In one embodiment, the member(s) may comprise a valve seat. A valve retaining formation may depend from the member, for example at the intersection with an additional member. The valve retaining formation may comprise a projection having a neck portion, about which the valve can typically be located, and a head portion, typically arranged to retain the valve. The valve retaining formation may comprise a spigot. The valve may have a mounting formation, such an opening which is larger in width than the neck but smaller than the head.

The connector of the present invention may accommodate a valve, in a manner which is not possible using the connector arrangement of FIG. 1.

The connector may be provided with a one way valve. The one way valve may comprise a valve seat. The valve seat may have a plurality of connected arms. The arms may be connected at a joint along a central axis of the connector. The arms may extend radially between the joint and an inner surface of the connector. There are preferably four, symmetrically disposed arms. The arms preferably lie in the plane of the connector. The valve seat may be adapted to receive a valve member or closure member. The valve member is preferably a piece of thin, flexible material. The valve member preferably occludes the gases passageway and is preferably circular in shape. The valve member may lie in the plane of the valve seat. The valve member may be in touching contact with a surface of the valve seat.

In some embodiments, the one-way valve may be located and/or mounted within the male connector. The valve member is preferably centrally mounted.

The inner surface of the female conduit may further comprise a generally axially extending depression, the axis typically being common to the male and female connector ends when connected. The depth of the depression may be between 0.1 and 0.5, typically between 0.2 and 0.4, of the thickness of the female conduit wall. The depression may extend generally axially from the end of the female conduit. Preferably, a plurality of such axially extending depressions is provided on the inner surface of the female connector wall. The depressions may be symmetrically disposed about the axis of the female conduit. The depressions may be generally trapezoidal in shape. An inner surface of the wall of the female connector may comprise a generally annular recess for receiving the retaining formation. The depressions may lead into, or form part of, the annular recess. The depression may extend in a direction substantially perpendicular to the annular recess.

Any of the first, second and/or combined conduit may define a flow passage in a first direction. Either or both of the first and second conduits may comprise a further conduit or port defining a further flow passage which is angularly offset from the first direction. The further flow passage may be oriented substantially perpendicularly relative to the first flow passage. The further port or conduit may provide a branch in the first or second conduit. The further port or conduit may comprise a connector formation for attachment to further device or duct. The further connector formation may comprise a swivel connector formation, which may be comprise any, or any combination, of the geometric features of male or female connector ends described above.

Either or both of the first and second conduits may each have first and second flow ports which may comprise any combination of inlet and/or outlet ports of the connector in use.

According to a second aspect of the invention there is provided a breathing circuit comprising the connector of the first aspect of the invention. In some embodiments, the breathing circuit may include a main gases passageway and a respiratory component which is connected, by the connector of the first aspect of the invention, to a port in the side wall of the main gases passageway. This is advantageous as the respiratory component can be rotated to a position, such that the connector advantageously remains in the position in which it is placed by the user. If, for example, the respiratory component comprises a manually adjustable valve, for attachment to a scavenger tube, the user can rotate the valve so that the scavenger tube either extends away from the patient, or does not interfere with treatment of the patient by a clinician.

Furthermore, the rotating connector of the invention provides an increased resistance to rotation relative to prior art rotating connectors. This increased resistance means that, in the example of an APL valve connector, rotating the cap of an APL valve, in order to adjust the quantity of gas allowed to escape from the circuit, does not cause the whole APL valve to rotate.

In other embodiments the breathing circuit may include a first or main gas passageway defined by two respiratory gas ducts connected together by the connector of the first aspect of the invention. The invention therefore would be particularly useful for mounting components for which stable rotational positioning is important.

An example of this would be a Mapleson breathing circuit, such as a Mapleson A or C breathing circuit. In this circuit, the reservoir bag is connected to the circuit by branched connection to the main passageway using, for example, using a T-connector having a passageway which can be connected in line with the main passageway of the circuit, and a port which extends radially away from the main passageway. A reservoir bag may be connected in line with the main passageway. If the T-connector is connected to the main passageway by rotating connectors according to the invention, a user is able to rotate the reservoir bag into a desired stable angular position, so that, for example the bag and/or tubing do not interfere with treatment.

According to a third aspect of the invention, there is provided a connector for connecting respiratory ducts together such that they are placed in fluid communication, the connector comprising a female connector member and a male connector member, the male connector member being adapted to be received within the female connector member and having a retaining formation which is adapted to resist separation of the female and male members, wherein the ratio of the diameter to the length of the plug is less than 1.4.

According to a further aspect of the invention, there is provided a connector for connecting respiratory ducts together such that they are placed in fluid communication, the connector comprising a female connector member and a male connector member, the male connector member being adapted to be received within the female connector member and having a retaining formation which is adapted to resist separation of the female and male members whilst permitting relative rotation thereof when connected, wherein the male and female connector members form a common conduit when assembled and the male or female connector member comprises a valve seat formation arranged within said conduit.

Preferably the valve seat formation is located in the portion of the male connector member which is insertable within the female connector member. The valve seat formation may be integrally formed with the male or female connector member.

Any of the preferable features described above in relation to any one aspect of the invention may be applied to any other aspect of the invention wherever practicable.

FIG. 2(a) to (c) relates to a male connector 2 of a rotating connector according to the invention. The male portion comprises a tubular gases passageway having first 4 and second 5 sections. The first 4 and second 5 sections each have a generally cylindrical cross-section. The inner surfaces of the first and second sections have generally the same radius. The outer surface of the first section has a slightly larger radius than the outer surface of the second section.

The second section 5 comprises a standard connector end for attachment to respiratory tubing or else, in the case of the present embodiment, a respiratory/reservoir bag as will be described below.

The first section is provided with a cylindrical port 25 projecting radially outwardly. The cylindrical port 25 allows access to, and thereby fluid communication with, the interior of the male connector 2.

The end of the first section 4 which is remote from the second section 5 is provided with an axially extending tubular plug 6 of circular cross-section, which may otherwise be referred to as a male connector end. The outer surface of the plug 6 has a smaller radius than the outer surface of the first section, so as to define a continuous annular shoulder 7 on the outer surface of the male connector 2. The radius of the plug 6 is substantially constant along its length. However the radius of the plug 6 at its base, i.e. in the region adjacent to the continuous annular shoulder 7, is very slightly larger than that of the remainder of the plug. The end of the plug remote from the first section is a free, open end in the unconnected state shown.

The outer surface of the plug 6 is provided, in a region close to the free end of the plug 6, with a retaining flange 8 and a sealing flange 9. Each of the flanges constitutes a narrow, slightly raised annular region of the outer surface of the plug. The height of each flange, i.e. the distance that the flange extends outwardly from the outer surface of the plug 6, is constant along the length of the flange. The width of each flange, i.e. the distance which the flange extends axially along the outer surface of the plug 6, is constant along the length of the flange. The retaining flange 8 is slightly narrower than, and has a slightly greater height than, the sealing flange 9. The sealing flange 9 is located very close to the free end of the plug. The retaining flange 8 is located between the sealing flange 9 and the continuous annular shoulder 7. The retaining flange 8 is located closer to the free end of the plug 6 than to the continuous annular shoulder 7, at approximately one-third of the way along the plug 6 from the free end. The distance between the retaining flange 8 and the continuous annular shoulder 7 is approximately 11 mm.

Figure 5:
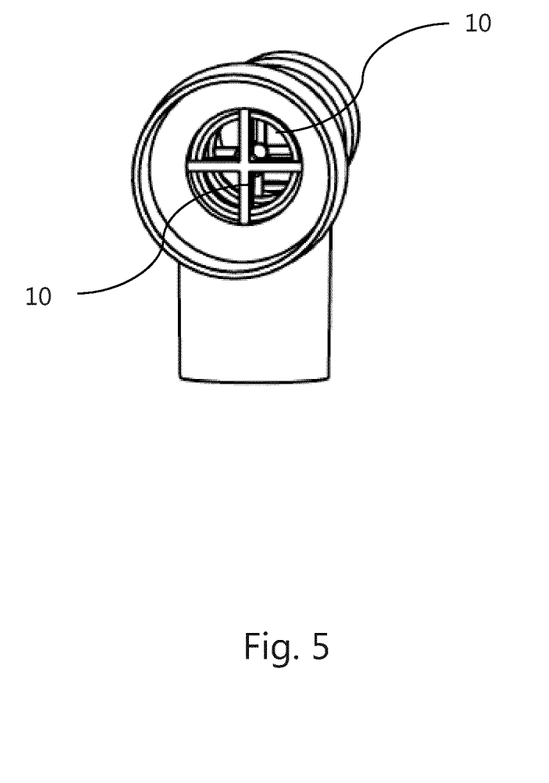
FIG. 5 is a further perspective view of the assembled connector of FIG. 4

A cross-shaped valve seat 10 is provided inside the plug 6 at the free end of the plug 6 (see FIG. 5). The cross-shaped valve seat 10 comprises four thin arms, each having a generally square cross-section, which extend radially outwards from a central junction to meet the inner surface of the plug. Alternatively, the cross-shaped valve seat 10 may be considered to comprise two arms extending across the full diameter of the plug. The arms all lie in the axial plane of the plug 6.

A spigot formation 10a is located centrally on the cross-shaped valve seat 10 for attachment of a valve member thereto.

The cross-shaped valve seat 10 is located generally at the end of the male connector 2. However, as can be seen in FIG. 2b, the seat is recessed slightly with respect to the end of the plug. In this regard, an annular projection 10b protrudes beyond the cross-shaped valve seat 10 at the plug end. The annular projection 10b depends inwardly from the internal wall of the male connector a short distance to define a central aperture which is co-axially mounted to the end of the plug 6. The annular wall 10b thus defines a peripheral wall for the valve seat and provides a slight restriction in the flow path through the connector at the valve seat.

A similar cross-shaped valve seat is found within the female part of the connector, although that valve seat may or may not have the annular wall feature.

Figure 3:
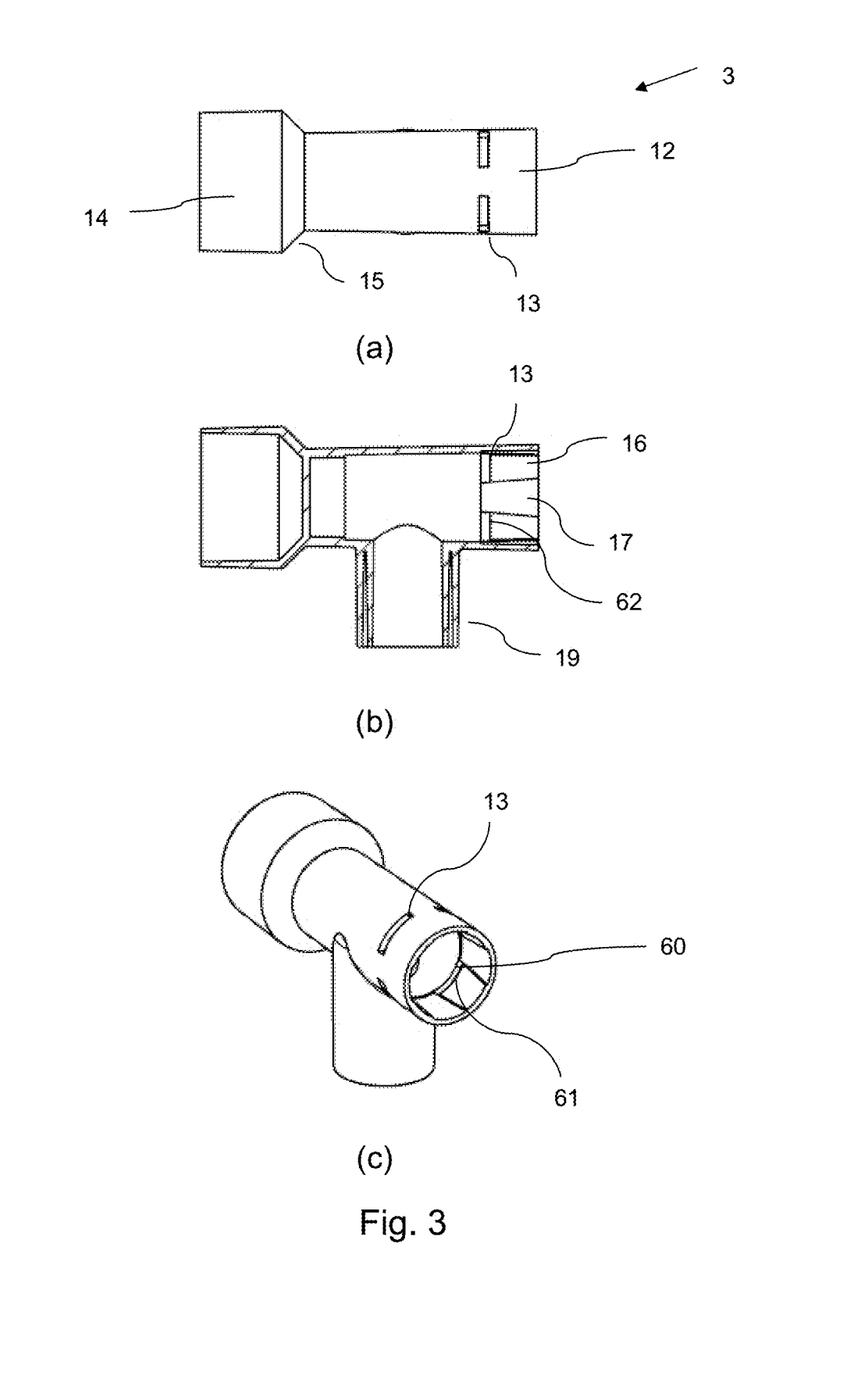
FIG. 3(a) to (c) shows the female part of a rotating connector according to the invention.

FIG. 3(*a*) to (*c*) relates to a female connector 3 of a rotating connector according to the invention. The female connector 3 comprises a generally cylindrical tube 12 defining a main gases passageway. A length of generally cylindrical tubing 14 having a larger radius than the main passageway is connected, by a bevelled section 15, to the distal end of the main passageway. The proximal end of the main passageway is open to the atmosphere although it may be connected to a further part of a respiratory system as will be described below.

In some embodiments, a port 19 is provided in the wall of the main passageway approximately mid way along its length. The port in such an embodiment may extend radially outwards from the main passageway. In this example, the port 19 comprises two, co-axially mounted, cylindrical collars. The collars are connected together by four spaced, axially-extending ribs (not shown) located between the collars. The outer collar has the same radius as the main passageway. The inner collar has a slightly smaller radius.

The port 19 in this embodiment thus provides for a conventional fixed or swivel connector. However it is intended that in other embodiments, the swivel connector at port 19 will take the form of the plug 6 of the male connector 2 as described above. However the port 19 will typically not comprise a valve seat at its free end since such a feature is not necessary at that location.

The inner surface of the free end of the main passageway is provided with four spaced, symmetrically disposed, axially-extending depressions or recesses 17. In other embodiments, it is envisaged that three or more such depressions may be provided. The depressions may be of reduced wall thickness or otherwise sunken relative to the internal surface of the female connector 3, for example in the cylindrical tube 12 thereof. The depressions may alternatively be of constant wall thickness and may be formed by increasing the wall thickness of the female part in surface portion 16 adjacent to the depressions. In any embodiment, the depressions or the surface portion 16 adjacent thereto may be ramped, for example such that the depth of the depressions reduces towards the free end of the main passageway.

The depressions 17 begin at the free end of the cylindrical tube 12 and extend generally axially, for example by a distance of approximately 12 mm. The proximal end of each depression 17 lies parallel to the distal end of each depression 17. Furthermore, the proximal end of each depression 17 is longer than the distal end, and the sides of the depression 17 are inclined relative to the axis of the female connector 3. The depression 17 is therefore generally trapezoidal in shape.

As the depressions 17 are symmetrically disposed and spaced, the presence of the depressions 17 means that the inner surface of the tube is raised in the regions between the depressions. In particular, surface portion 16 is generally trapezoidal in shape and is generally symmetrically disposed about the axis of the female connector 3. These raised portions shall be referred to as leading walls.

A generally rectangular window 13 is provided in the side wall of the female connector 3 in the region of the distal end of each surface portion (or leading wall) 16. The generally rectangular window 13 has two longer sides and two shorter sides. The longer sides extend in the plane of the connector 3, while the shorter sides extend generally axially. As the rectangular window 13 is aligned with the surface portion (leading wall) 16, window 13 is located between two depressions 17 of the tube wall. The window is thus located at the end of a corresponding surface portion (leading wall) 16.

Figure 7:
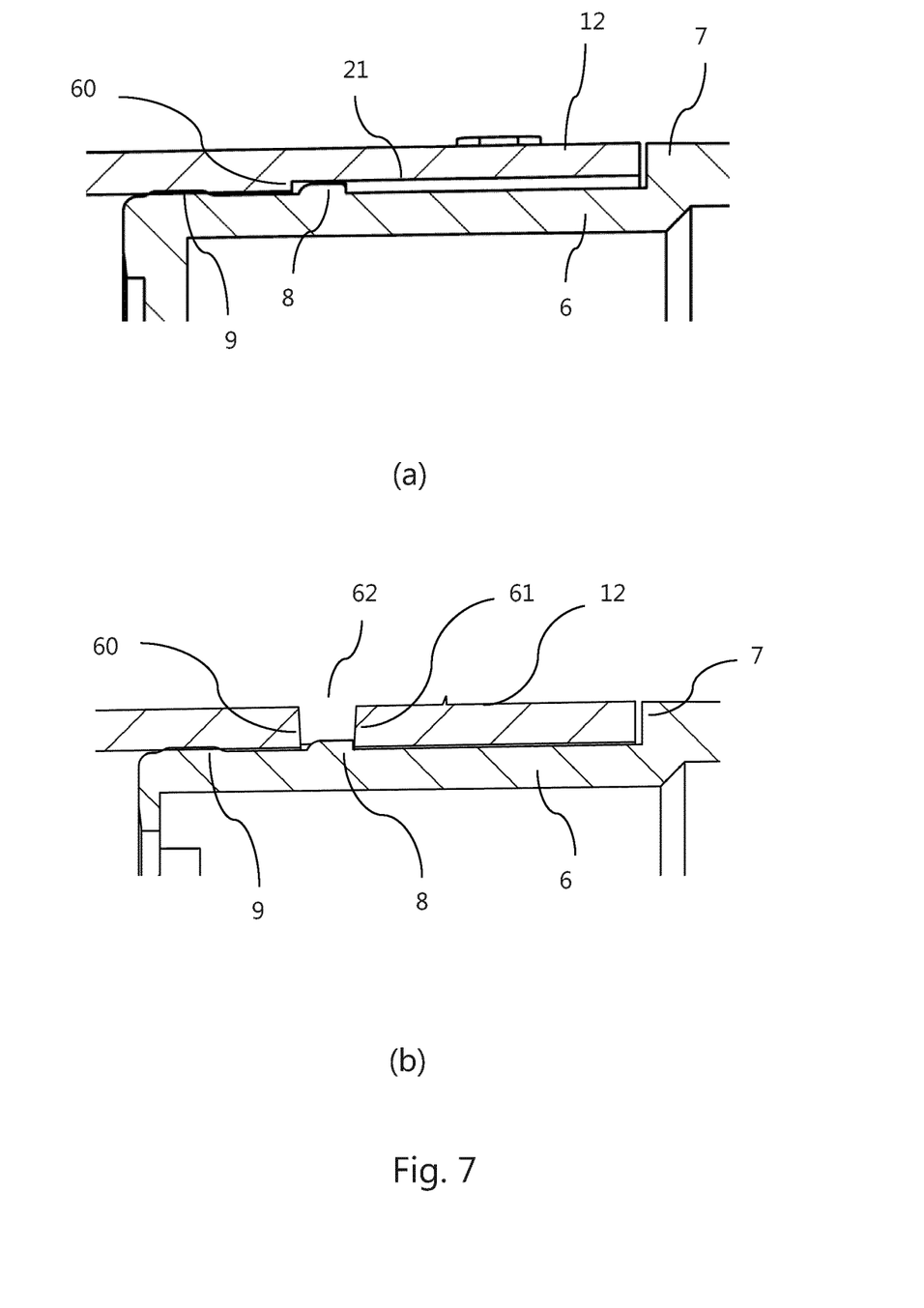

An annular groove or recess 62 is provided in the female connector 3 and serves as a retaining formation for the male part in use. The groove 62 is of short axially-extending length relative to the tubular passageway. The inner surface of the wall in this annular groove 62 is recessed, the sides of the groove 62 being defined on one side by a continuous shoulder 60 and on the other side by a discontinuous shoulder 61 defined by the ends of the leading walls. This can be seen in FIGS. 7(*a*) and (*b*) which show cross-sections of the assembled connector in a plane which does not contain a window (FIG. 7(*a*)) and in a plane which does contain a window (FIG. 7(*b*)). The depressions 17 thus run into and/or form part of the groove 62.

The rectangular window 13 is provided in the annular groove 62 and is aligned therewith. That is to say the window extends in an annular direction and are of width equal to the width of the groove 62. Thus the groove 62 is effectively formed by the end portion of depressions 17 and the window spaced therebetween.

The main passageway of the female part is flared, in other words, the opening at the proximal end is larger than the opening at the distal end. As the plug 6 is inserted into the female part the side wall of the main passageway applies an increasing compressive force to the retaining flange 8 on the plug 6. This force causes the retaining flange 8 to resiliently deform into a stressed configuration. Further insertion of the male connector 2 causes the open end of the female connector 3 to abut the continuous annular shoulder 7 of the male connector 2. At this point, the retaining flange 8 has reached the annular groove 62. This means that the compressive affect of the inner surface of the main passageway on the retaining flange 8 is removed, allowing the resilience of the flange 8 to cause it to return to its rest configuration. If a user attempts to withdraw the male connector 2 from the female connector 3, the retaining flange 8 abuts the continuous annular shoulder 7 on the inner surface of the female connector 3, formed by the surface portion (leading wall) 16. This abutment impedes withdrawal. Although the abutment does not prevent the male connector 2 from rotating relative to the female connector 3, there is sufficient resistance to rotation that if a user were to give the male connector 2 a particular orientation relative to the female connector 3, the connector 1 would remain in that orientation.

The close fitment of the retaining flange in the annular groove has been found to provide an advantageous sealing effect, which prevents or substantially restricts flow through windows 13 at normal operating pressures for a respiratory circuit. However in this embodiment, the sealing ring 9 has been found to further that sealing effect such that no additional sealing formations of materials are required.

By a similar mechanism to that described above, the flared shape of the main passageway means that insertion of the plug 6 into the female connector 3 causes compression of the sealing flange 9. With the plug 6 fully inserted, the sealing flange 9 is therefore compressed by the sidewall of the female connector, providing an effective seal.

Figure 4:
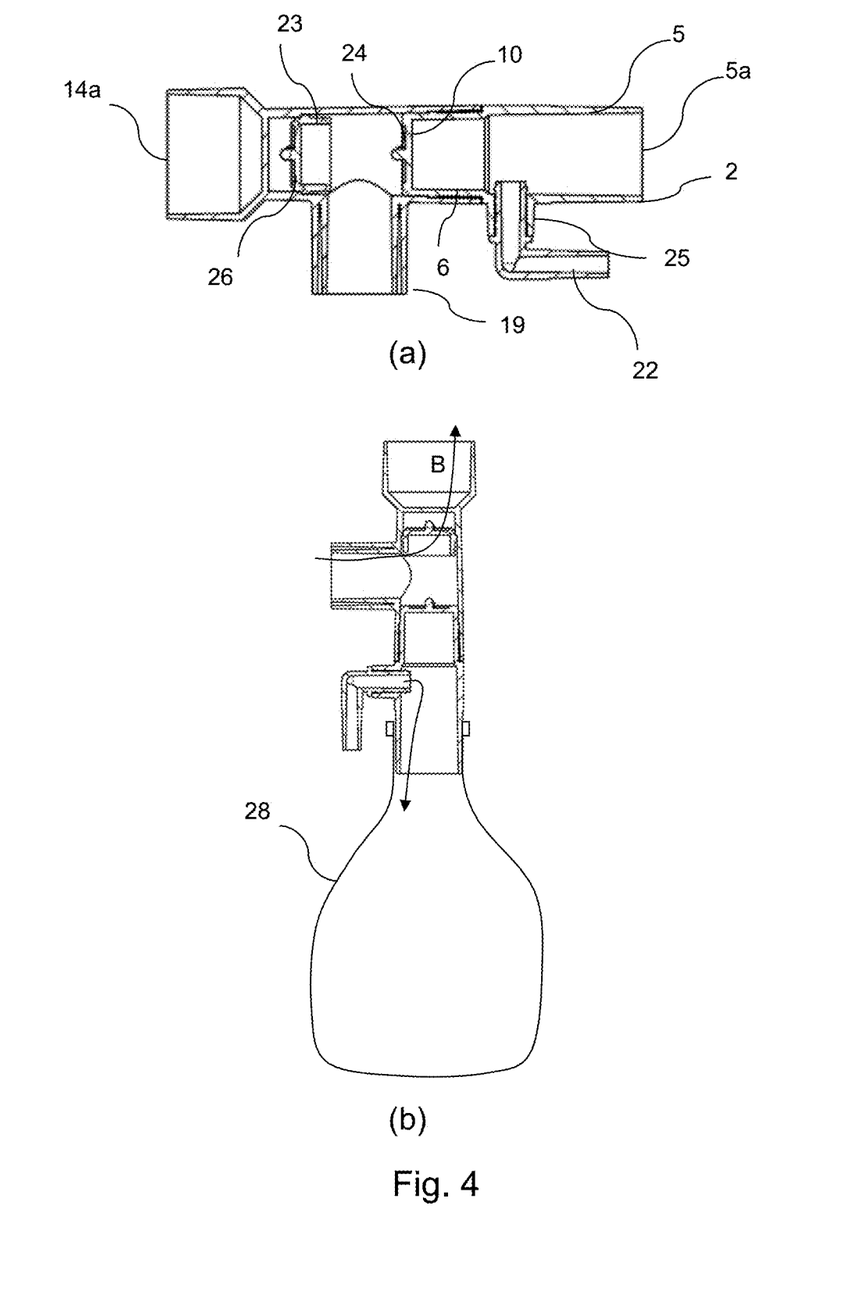

FIGS. 4(*a*) and (*b*) show the assembled connector. It can be seen that once assembled, the cross-shaped valve seat 10 of the male connector 2 terminates within the female connector 3, a short distance from the opening of the port 19, typically in an upstream direction in an inspiratory flow direction. Also it can be seen that a valve seat 23 is located part way along the main flow passage of the female connector. That valve seat formation is located between the port 19 and the end section of cylindrical tubing 14. The valve seat 23 is substantially the same in construction as the cross-shaped valve seat 10 described above and will not be described again for conciseness.

When assembled as shown in FIG. 4*a*, the valve seats in each of the male and female connector parts are arranged in series, one on each side of the port 19.

A generally linear or axial flow passage is defined from the end 5*a* of male portion of the assembled connector to the opposing end 14*a* of the female portion. That flow path is interrupted by the valve seats of each of the male and female connectors which are both perpendicular to the flow path.

Disc shaped valve members 24 and 26 are located on, and retained by, the spigot or stem formation on each valve seat. Each valve member 24, 26 is resiliently deformable between a closed condition in which it lies against the valve seat and an open condition, in which it is angularly displaced under fluid pressure in the respiratory system. The resilience of each valve member biases it towards its at-rest, or closed, condition.

The cylindrical port 25 of the male connector provides a connection for a standard respiratory gas delivery tube 22, through which gas for inhalation by the patient is delivered under a positive pressure from conventional gas delivery equipment, which is known to a person skilled in the art. The delivered gas may comprise, for example, an anesthetic gas, such as nitrous oxide. The delivered gas may additionally or alternatively comprise oxygen. The gas may be a mixture of 50% nitrous oxide and 50% oxygen.

A reservoir bag 28 of conventional design, such as a 2-liter capacity bag, is attached to section 5 of the exposed end 5*a* of the male connector. The port 19 is connected directly or indirectly to a patient interface device, such as for example a respiratory mask or mouthpiece. The exposed end 14*a* of the female connector portion may be open to the atmosphere but typically provides for connection to a conventional respiratory gas scavenging system as will be understood by a person skilled in the art. Accordingly the exposed end 14*a* is shaped to provide a conventional tube connector formation.

In use, respiratory gas is supplied under positive pressure via tube 22 to the interior of the connector via cylindrical port 25 of male connector 2. The one-way valve 24 is closed at rest and thus the delivered gas fills the bag 28 to provide a ready volume of gas for delivery to the patient. During inspiration, the negative pressure applied by the patient and/or positive gas delivery pressure causes gas to flow from the inlet and/or bag 28 to the patient via valve 24 and port 19.

During expiration, a positive pressure is applied at port 19 and the direction of flow in port 19 reverses such that the expired flow re-enters the connector. However the one-way valve 24 prevents passage of the expired flow into the male connector 2 of the connector. The positive pressure in the interior of the valve causes the one way valve 26 to open and thereby allow the expired gas to exit the connector in the direction of arrow B via outlet end port 14*a* and pass to a scavenging system.

Figure 6:
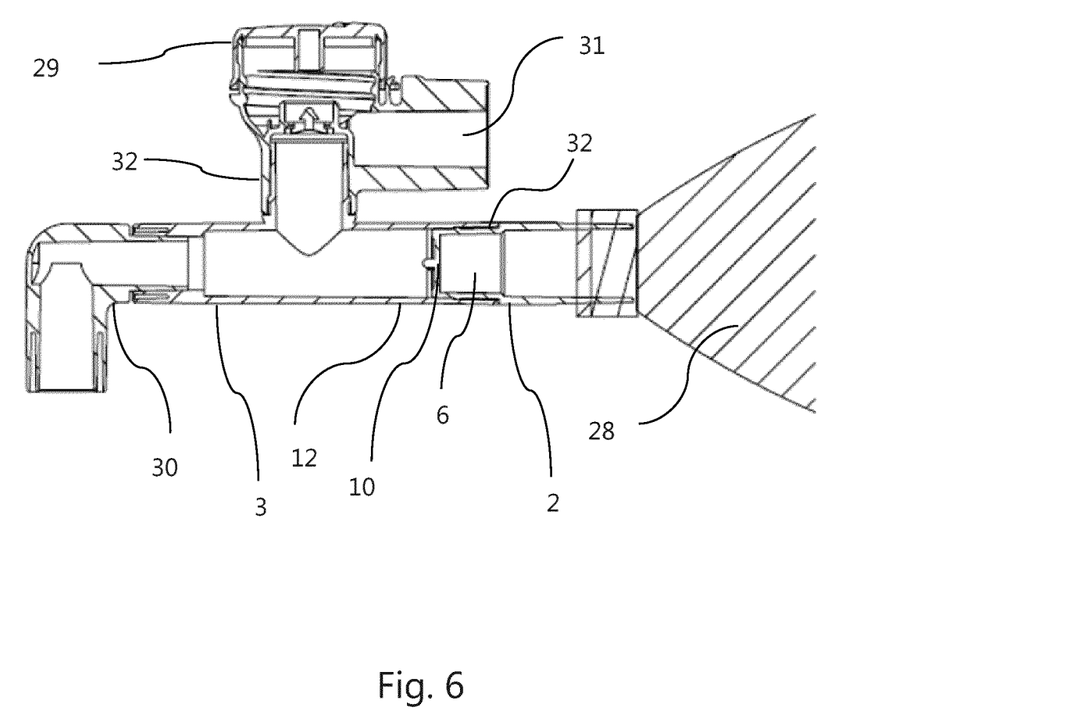
FIG. 6 shows a longitudinal section through a Mapleson C breathing circuit connector according to the invention in use; and, FIG. 7(a) shows a partial section of the assembled connector in a plane which does not contain a window in the female connector.

Turning now to FIG. 6, there is shown a cross-section of a Mapleson C breathing circuit connector assembly containing male and female rotating connector portions substantially as described above. The circuit comprises a main cylindrical tube 12, reservoir bag 28, Adjustable Pressure Limiting (APL) valve 29 and elbow connector 30. The elbow connector 30 leads to a patient interface (not shown). The cross-shaped valve seat 10 is located within the main tube. However in this embodiment, the further valve seat 23 and valve member 26 are absent. Also the end of cylindrical tubing 14 of the female connector 3 is configured for attachment to a standard patient interface connector, instead of the scavenging connector end 14a of the above embodiments.

The general function of this type of circuit is known and will not be discussed in further detail here. The purpose of the APL valve 29 is to allow exhaled gases to escape from the circuit. The exhaled gases may escape directly from the outlet 31 to the atmosphere. Alternatively, an end of a scavenger tube (not shown) may be attached to the outlet 31. The other end of the scavenger tube is connected to a suction pump. The suction pump acts to force exhaled gases out of the circuit via the scavenger tube.

Figure 2:
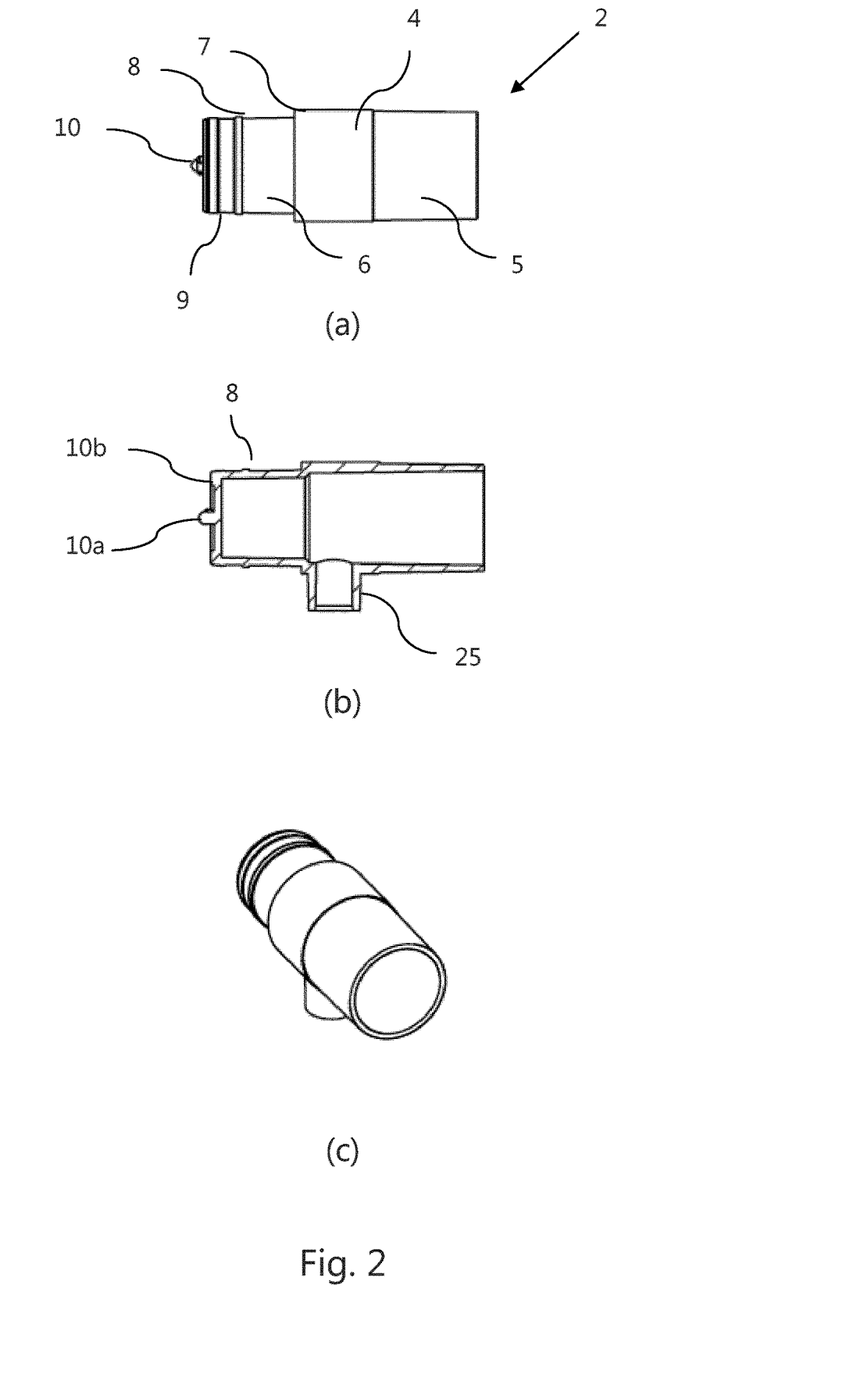
FIG. 2(a) to (c) shows the male part of a rotating connector according to the invention.

The connections made at locations 32 in FIG. 6 (i.e. at the connection between the male and female connector portions and/or at the connection between the port 19 of the female connector and the APL valve 29) are as described above with reference to FIG. 7 and the connection formed between the male and female components of FIGS. 2-4.

As shown in FIG. 6, if the APL valve 29 is connected to the main cylindrical tube 12 using a rotating connector according to the invention, this rotating connection allows the user to rotate the valve 29 such that, for example, the gases leaving the outlet 31 of the valve 29 are directed away from the care provider. If a scavenger tube is present, the user can rotate the valve 29 so that the scavenger tube either extends away from the patient, or does not interfere with treatment of the patient by a clinician. In both these cases the connector advantageously remains in the position in which it is placed by the user.

Furthermore, as noted above, the rotating connector provides an increased resistance to rotation relative to prior art rotating connectors. This increased resistance means that rotating the cap of an APL valve 29 in order to adjust the quantity of gas allowed to escape from the circuit does not cause the whole APL valve 29 to rotate.

A connector according to the invention may additionally or alternatively provide a safety benefit in that it can inhibit detachment of the APL in transit, which can occur for example due to accidental impact or other mishandling of the device.

Whilst specific embodiments and intended uses of the invention have been described above, it is to be noted that such embodiments are not intended to be exhaustive and there exist other locations and uses within a respiratory system, in which the connector according to the invention may be employed to achieve a stable rotating connection. In all such embodiments, the male and female connector portions are sized so as to cause a frictional engagement between the walls thereof which is a close fit such that the frictional engagement resists relative reorientation of those parts in normal use (for example under the loading caused by contorted tubes or the like) but permits reorientation under a manually applied torque or relative twisting action. Accordingly the fitment between the male and female connector parts is different to an interference fit, in which engagement between two parts is formed by the deformation of one part in contact with another so as to form a tight, jamming relationship there-between. In contrast the contact between the male and female connector parts of the present invention provides a touching, but not deforming, contact once assembled, save for at one or more sealing formations, where only a slight contacting pressure is applied.

It has been found that the feel of the tight-fitting, but swivelling, connector parts according to the invention can also serve to ensure an operator that the connection formed thereby is airtight and safe. In contrast, operators who have been used to fixed, non-swivelling connectors, have been found to question the integrity of a freely swivelling connection according to the prior art and interpret the movement of the connector as being indicative of a faulty or loose connection.

In any embodiment, the male and/or female connector parts can be moulded, typically by injection moulding, thereby integrally forming all of the features described above in relation to FIG. 2 and/or FIG. 3. A conventional plastic material may be used. The male and female components may be formed separately. The male and female components may be formed concurrently in separate mould cavities within a common moulding tool.

The invention claimed is:

1. A connector for connecting respiratory ducts together such that they are placed in fluid communication, the connector comprising:
   a first conduit having a female connector end; and
   a second conduit having a male connector end adapted to be received within the female connector end of the first conduit such that the male and female connector ends overlap to provide a common conduit having an inner surface formed at least in part by the male connector end,
   wherein the male connector end has a retaining formation which is adapted to abut a corresponding engagement formation on an overlapping portion of the female connector end so as to resist separation of the first and second conduits whilst permitting relative rotation thereof when connected,
   and wherein the engagement formation comprises an annular recess on an inner surface of the female connector end shaped to accommodate the retaining formation with a close fit, and the inner surface of the overlapping portion of the female connector end comprises a plurality of depressions and raised portions in the regions between the depressions, the plurality of depressions and raised portions extending in a direction substantially parallel with an axis of the first conduit, the depressions leading into the annular recess.

2. A connector according to claim 1, wherein the depth of the depressions varies with distance from the end of the retaining or engagement formation.

3. A connector according to claim 1, wherein an annular gas seal is formed between the inner surface of the female connector end and the opposing outer surface of the male connector end.

4. A connector according to claim 3, wherein the male connector end comprises first and second annular projections spaced along its length, the first projection comprising the retaining formation and the second projection comprising a sealing formation.

5. A connector according to claim 4, wherein the second projection is provided at a distal end of the male connector.

6. A connector according to claim 1, wherein the male connector end comprises at least one annular projection, said projection providing the retaining formation and/or a sealing member between the male and female connector ends.

7. A connector according to claim 1, wherein the ratio of the diameter to the length of the male connector end received within the female connector end is less than 1.4.

8. A connector according to claim 7, wherein the length of the male connector end received within the female connector end is substantially equal to its diameter.

9. A connector according to claim 1, wherein the male connector end has an end stop formation projecting radially outwardly from the surface of the male connector end so as to limit the extent to which the male connector end can extend into the female connector end.

10. A connector according to claim 1, wherein the male connector end has one or more members spanning the flow path of the second conduit and/or spanning the flow path of the first and second conduits when the first and second conduits are in a connected configuration.

11. A connector according to claim 10, wherein the member is integrally formed with the male connector end, typically in the portion of the male connector end which is inserted into the female connector end.

12. A connector according to claim 10, wherein the member comprises a valve seat, the valve seat having a mounting formation for a valve member, said valve member being resiliently actuable relative to the valve seat in use.

13. A connector according to claim 1, wherein the common conduit defines a flow passage in a first direction and either or both of the first and second conduits comprise a port defining a further flow passage which is angularly offset from the first direction.

14. A connector according to claim 13, wherein the port comprises a branch duct which is integral with the first or second conduit and rotatable therewith about an axis of the common conduit.

15. A connector according to claim 1, wherein one of the first and second conduits comprise a connector formation for attachment to a deformable reservoir bag and the other of said conduits provides an outlet port and/or connector formation.

16. A connector according to claim 1, wherein the female and male connector ends form a tight fit along the length of the overlapping portion of the female connector end.

17. A connector according to claim 1, wherein the annular recess is provided on the inner surface of a tubular section of the female connector end and extends around the retaining formation of the male connector end when received in the female connector end.

18. A connector according to claim 1, wherein the retaining formation on the male connector end and the corresponding engagement formation on the female connector end are in frictional contact, and wherein a surface of each of the raised portions on the inner surface of the female connector end is held in frictional contact with an outer surface of the male connector end while the first and second conduits are in fluid communication.

19. A respiratory duct assembly comprising the connector of claim 1, wherein the common conduit provides a flow passage in a first direction, the assembly further comprising a respiratory component connected to a port in either of the first and second conduits.

20. A respiratory duct assembly according to claim 19, wherein the respiratory component comprises any or any combination of a reservoir bag, a respiratory gas delivery tube, an adjustable valve, a gas scavenging duct and/or a patient interface device.

21. A respiratory duct assembly according to claim 20, wherein the adjustable valve comprises a valve adjustment mechanism which is rotatably adjusted by manual input.

* * * * *